US00PP34603P2

(12) United States Plant Patent
Smit

(10) Patent No.: US PP34,603 P2
(45) Date of Patent: Sep. 20, 2022

(54) ***PEPEROMIA* PLANT 'EC-PEPE-2101'**

(50) Latin Name: *Peperomia caperata*
Varietal Denomination: EC-PEPE-2101

(71) Applicant: Eden Collection, BV, Sappemeer (NL)

(72) Inventor: Obed Smit, Sappemeer (NL)

(73) Assignee: Eden Collection B.V.

( * ) Notice: Subject to any disclaimer, the term of this patent is extended or adjusted under 35 U.S.C. 154(b) by 0 days.

(21) Appl. No.: 17/677,265

(22) Filed: Feb. 22, 2022

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Cassandra Bright

(57) ABSTRACT

A new and distinct cultivar of *Peperomia* plant named 'EC-PEPE-2101' is disclosed, characterized by round, glossy, bluish-grey leaves with deep veins. The new variety is a *Peperomia*, typically used as an ornamental plant.

3 Drawing Sheets

Latin name of the genus and species: *Peperomia caperata.*

Variety denomination: 'EC-PEPE-2101'.

BACKGROUND OF THE INVENTION

The new cultivar is a product of a planned breeding program to produce distinct and better performing *Peperomia* varieties. The new variety was selected as a seedling resulting from the crossing of *Peperomia caperata* '#012', and '#017', two unpatented varieties from the inventor's breeding line. The crossing was made by the inventor, Obed J. Smit, a citizen of the Netherlands in 2018. 'EC-PEPE-2101' was selected by the inventor in 2020 at a commercial greenhouse in Sappemeer, the Netherlands.

Asexual reproduction of the new cultivar 'EC-PEPE-2101' by terminal cuttings was first performed in Sappemeer, the Netherlands at a commercial greenhouse in March 2020, and has shown that the unique features of this cultivar are stable and reproduced true to type through successive generations.

SUMMARY OF THE INVENTION

The cultivar 'EC-PEPE-2101' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-PEPE-2101'. These characteristics in combination distinguish 'EC-PEPE-2101' as a new and distinct *Peperomia* cultivar:

1. Round glossy bluish grey leaves with deep veins.
2. Very compact growing, well suited for small pots.
3. Unique bluish grey tint of the leaves.

PARENT COMPARISON

Plants of the new cultivar 'EC-PEPE-2101' are similar to plants of the female parent, *Peperomia caperata* '#012' in most horticultural characteristics, however, plants of the new cultivar 'EC-PEPE-2101' differ from in the following characteristics:

1. Leaves of the new variety are round-shaped, while leaves of the seed parent are less rounded with a pointed tip.
2. Leaves of the new variety are glossy and bluish-grey on the upper side, while leaves of the seed parent are paler grey.
3. Leaves of the new variety have deep-lying, dark-green veins, while leaves of the seed parent are not deep.
4. Leaves of the new variety are puckered, while leaves of the seed parent are smooth.

Plants of the new cultivar 'EC-PEPE-2101' are similar to plants of the male parent, *Peperomia caperata* '#017' in most horticultural characteristics, however, plants of the new cultivar 'EC-PEPE-2101' differ in the following characteristics:

1. Leaves of the new variety are glossy and bluish-grey on the upper side deep-lying, dark-green veins, while leaves of the pollen parent are a dull, dark-green.
2. Growth habit of the new variety is much more compact than that of the pollen parent.

COMMERCIAL COMPARISON

Plants of the new cultivar 'EC-PEPE-2101' are similar to plants of the commercial variety *Peperomia* 'Eden Rosso', U.S. Plant Pat. No. 24,379. However, plants of the new cultivar differ in the following characteristics:

1. Leaf upper side of the new variety is glossy bluish-grey with dark-green veins. Leaf upper side of this comparator is dark-green.
2. Leaf under side of the new variety is grey-green with red veins, while leaf under side of this comparator is red.
3. Leaves of the new variety are round-shaped, while leaves of this comparator are oblong with a pointed tip.

Plants of the new cultivar 'EC-PEPE-2101' are similar to plants of the commercial variety *Peperomia* 'Napoli Nights', U.S. Plant Pat. No. 29,416. However, plants of the new cultivar differ in the following characteristics:

1. Leaves of the new variety are round-shaped, while leaves of this comparator are oblong with a more pointed tip.
2. Leaf upper side of the new variety is glossy bluish-grey with dark-green veins. Leaf upper side of this comparator is grey.
3. Leaf stems of the new variety are shorter than leaf stems of this comparator.

BRIEF DESCRIPTION OF THE PHOTOGRAPHS

The accompanying photograph in FIG. 1 illustrates in full color a typical blooming plant of 'EC-PEPE-2101' grown in a greenhouse. The plant is approximately 30 weeks of age.

Figure 1:
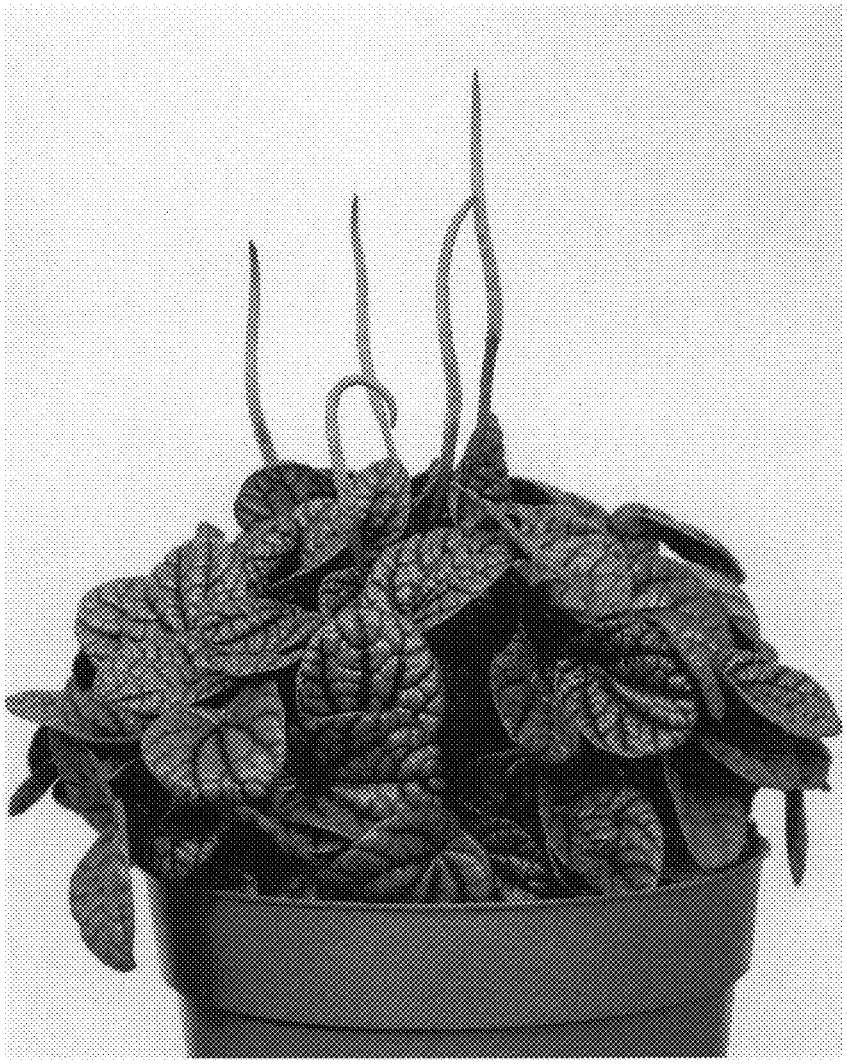
Figure 2:
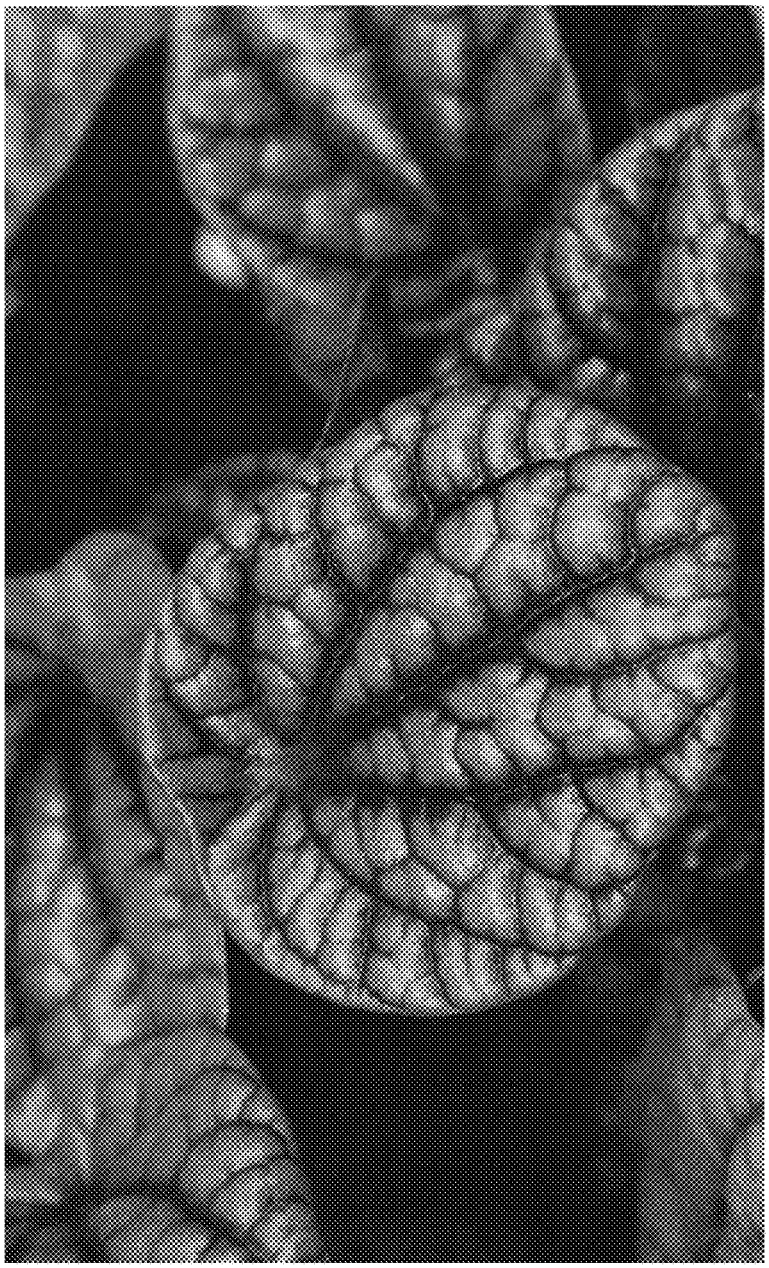
FIG. 2 illustrates a close up of the foliage.
Figure 3:
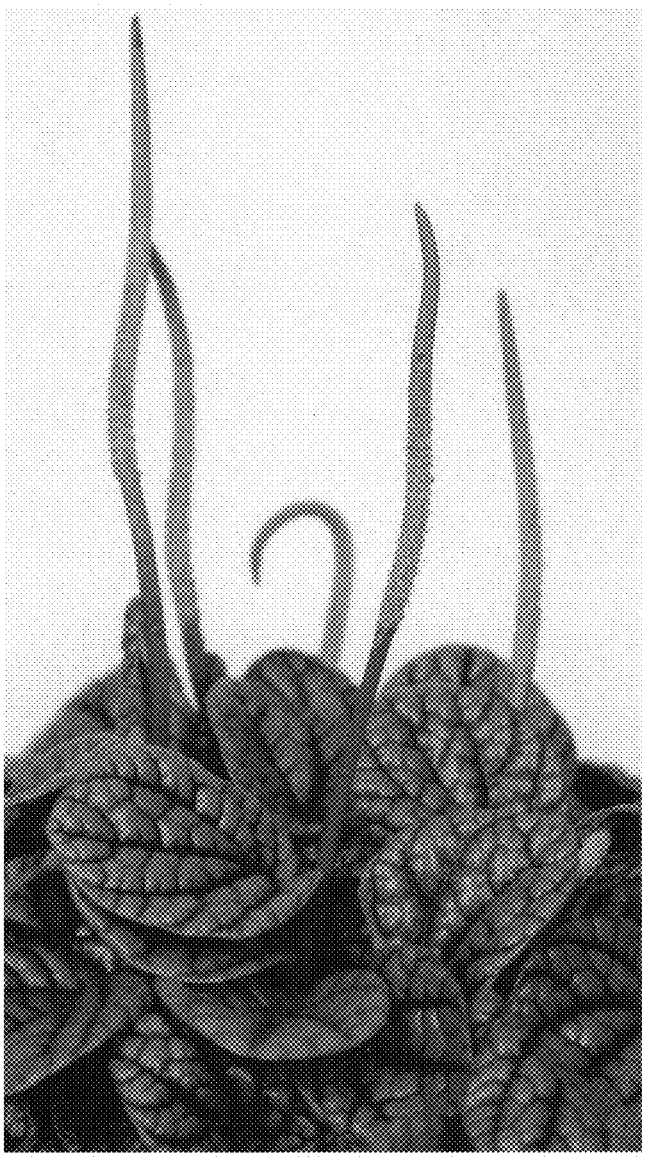
FIG. 3 illustrates a close up of inflorescences.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'EC-PEPE-2101' plants at 10 months of age, grown in a greenhouse in Sappemeer, the Netherlands during December. The growing temperature ranged from 17° C. to 20° C. at night to 19° C. to 21° C. during the day. Measurements and numerical values represent averages of typical flowering types.

Botanical classification: *Peperomia caperata* 'EC-PEPE-2101'.

PROPAGATION

Time to initiate roots: About 21 days at approximately 20° C. in summer.

Time to produce rooted cutting: About 25 days at 20° C. in summer.

Description of roots: Fibrous, fine, moderately dense, freely branching. White in color, not accurately measured with R.H.S. chart.

PLANT

Plant type: Perennial potted plant.

Plant shape: Flattened globular with inflorescences carried slightly above foliar plane.

Growth habit: Rosettes of leaves, forming very short, thick stems.

Plant spread: Approximately 18.9 cm.

Height: 11.3 cm to top of foliar plane; 19 cm to top of floral plane.

Growth rate: Moderate.

Plant vigor: Moderate.

Age of plant described: Approximately 10 months.

Branching habit: Leaves in rosettes, eventually forming very short, thick stems, branching into lateral rosettes of leaves.

Pinching: Pinching not required.

Number of primary (main) branches per plant: Average 14.

Number of secondary (lateral) branches per plant: Average 7.

Main branches:

*Length*.—Average: 1.9 cm.

*Diameter*.—Average: 0.5 cm.

Internode length: Average: Less than 0.1 cm.

Appearance and shape: Succulent, thick and rounded.

Luster: Matte.

Aspect/angle from vertical: Average angle: 20°.

Strength: Moderately strong.

Color:

*Developing*.—RHS Yellow-Green 146D.

*Mature*.—RHS Yellow-Green 146D.

*At internodes*.—RHS Yellow-Green 146D.

Pubescence: None.

Plant fragrance: None.

FOLIAGE

Leaf:

*Arrangement*.—Alternate, single.

*Quantity*.—Average 19.

*Average length*.—3.9 cm.

*Average width*.—3.5 cm.

*Shape of blade*.—Broad ovate, perfoliate.

*Apex*.—Obtuse.

*Base*.—Truncate.

*Margin*.—Entire, very slightly revolute.

*Texture of top surface*.—Glabrous, smooth, moderately leathery, slightly to moderately bullate.

*Texture of bottom surface*.—Glabrous, smooth, moderately leathery.

*Pubescence*.—None.

*Luster, upper side*.—Glossy.

*Luster, under side*.—Matte, velvety.

*Color*.—Young foliage upper side: RHS Yellow-Green 147B, veined Greyed-Orange 166A. Young foliage under side: RHS Yellow-Green 148D, veined Greyed-Purple 183C and 183D. Mature foliage upper side: A color between RHS Greyed-Green N189C and Black 202B; area surrounding veins Greyed-Green N189A, and slightly darker. Mature foliage under side: RHS Yellow-Green 147D, area surrounding veins Greyed-Red 182A.

*Venation*.—Pattern: Parallel, furrowed. Venation color upper side: RHS Greyed-Green N189A, and slightly darker. Venation color under side: RHS Greyed-Purple 183A.

*Petiole*.—Average Length: 6.7 cm. Diameter: 0.3 cm. Texture: Glabrous, smooth. Luster: Both sides very slightly glossy. Strength: Low. Color, upper side: RHS Yellow-Green N148B, moderately finely-striped Greyed-Red 182A, slightly more densely toward distal end. Color, under side: RHS Yellow-Green N148B, moderately finely-striped Greyed-Red 182A, slightly more densely toward distal end.

FLOWER

Inflorescence:

*Arrangement*.—Axillary spike.

*Inflorescence type and form*.—Spike.

*Inflorescence height*.—Average: 5.9 cm (excluding peduncle).

*Inflorescence diameter*.—Average: 0.3 cm.

*Quantity of flowers per inflorescence*.—Average 650 individual flowers per spike.
*Quantity of flowers per plant*.—Average 1,500.
*Quantity of flower buds per plant*.—Average 7,500.
*Quantity of flowers and buds per plant*.—Average 9,000.
*Natural flowering season*.—Fall into late spring.

Flower bud:
*Flower bud length*.—0.4 mm.
*Flower bud diameter*.—0.4 mm.
*Flower bud shape*.—Flattened, circular.
*Flower bud texture*.—Glabrous, smooth, slightly velvety.
*Flower bud luster*.—Slightly glossy.
*Flower bud color*.—Near RHS Yellow-Green 148C to 148D, slightly tinged near Greyed-Purple 184A.

Flower:
*Flower type and form*.—Individual flowers are very small and consist of 1 bract, 2 stamens and a single pistil.
*Flower aspect*.—Outward.
*Flowering habit*.—Very freely.
*Fragrance*.—None.
*Flower shape*.—Rotate, consisting of 1 bract, 2 stamens and 1 pistil only; no petals and sepals present.
*Flower height*.—Average: 1.2 mm.
*Flower diameter*.—Average: 0.9 mm.
*Flower length*.—Average: 0.8 mm.
*Flower longevity on plant*.—Average one month.
*Persistent* of *self-cleaning*?.—Self-cleaning.

Peduncles:
*Terminal peduncle length*.—Average 9.1 cm (from lowest individual flower to base).
*Terminal peduncle diameter*.—Average 3.0 mm.
*Peduncle angle to lateral branch axis*.—Average angle 30°.
*Peduncle strength*.—Weak.
*Peduncle texture*.—Glabrous, smooth.
*Peduncle luster*.—Moderately glossy.
*Peduncle color*.—RHS Yellow-green 147D, heavily finely striped Greyed-Red 182A.

Floral bracts:
*Quantity per flower*.—One below each individual flower.
*Shape*.—Orbicular.
*Length*.—0.6 mm.
*Width*.—0.6 mm.
*Color*.—Near RHS Yellow-Green 148D, very slightly tinged near Greyed-Purple 184C.

REPRODUCTIVE ORGANS

Stamens:
*Number*.—Average 2.
*Filament length*.—Average 0.7 mm.
*Filament color*.—Near RHS Yellow-Green 148C.

Anther:
*Shape*.—Ovate.
*Length*.—Average 0.2 mm.
*Width*.—Average 0.15 mm.
*Color*.—Near RHS Green-White 157A.
*Pollen*.—Low.
*Pollen color*.—Near RHS White 155A.
*Pistil*.—Number: Average 1. Length: Average 0.5 mm.
*Stigma*.—Shape: Flattened, circular. Length: Average 0.1 mm. Diameter: Average 0.2 mm. Color: Near RHS Yellow-Green 148C. Style: Sessile. Ovary color: Near RHS Yellow-Green 148C.

OTHER CHARACTERISTICS

Seeds and fruits: None observed to date.
Disease/pest resistance: No increased nor decreased resistance nor susceptibility to normal diseases and pests of *Peperomia* has been observed.
Temperature tolerance: Tolerates temperatures up to 40° C. Hardy to USDA zones 10 to 2.

What is claimed is:

1. A new and distinct cultivar of *Peperomia* plant named 'EC-PEPE-2101' as herein illustrated and described.

* * * * *